US009658192B2

(12) United States Patent
Guan et al.

(10) Patent No.: US 9,658,192 B2
(45) Date of Patent: May 23, 2017

(54) INSULATION DEFECT DETECTION OF HIGH VOLTAGE GENERATOR STATOR CORE

(71) Applicants: Xuefei Guan, Princeton, NJ (US); Jingdan Zhang, Plainsboro, NJ (US); Shaohua Kevin Zhou, Plainsboro, NJ (US); Mark W. Fischer, Pittsburgh, PA (US); Waheed A. Abbasi, Murrysville, PA (US); Scott A. Karstetter, Monroeville, PA (US); Christopher John William Adams, Pittsburgh, PA (US)

(72) Inventors: Xuefei Guan, Princeton, NJ (US); Jingdan Zhang, Plainsboro, NJ (US); Shaohua Kevin Zhou, Plainsboro, NJ (US); Mark W. Fischer, Pittsburgh, PA (US); Waheed A. Abbasi, Murrysville, PA (US); Scott A. Karstetter, Monroeville, PA (US); Christopher John William Adams, Pittsburgh, PA (US)

(73) Assignees: Siemens Corporation, Iselin, NJ (US); Siemens Energy, Inc., Orlando, FL (US)

( * ) Notice: Subject to any disclaimer, the term of this patent is extended or adjusted under 35 U.S.C. 154(b) by 794 days.

(21) Appl. No.: 13/742,615

(22) Filed: Jan. 16, 2013

(65) Prior Publication Data

US 2013/0191041 A1 Jul. 25, 2013

Related U.S. Application Data

(60) Provisional application No. 61/589,425, filed on Jan. 23, 2012.

(51) Int. Cl.
*G01N 27/82* (2006.01)
*G01N 27/90* (2006.01)
(Continued)

(52) U.S. Cl.
CPC .......... *G01N 27/904* (2013.01); *G01R 31/34* (2013.01); *G06F 17/11* (2013.01); *G01N 27/20* (2013.01);
(Continued)

(58) Field of Classification Search
CPC ...... G01N 27/00; G01N 27/20; G01N 27/205; G01N 27/904
(Continued)

(56) References Cited

U.S. PATENT DOCUMENTS 4,996,486 A 2/1991 Posedel
5,341,095 A 8/1994 Shelton et al.
(Continued)

FOREIGN PATENT DOCUMENTS

GB 2109112 A 5/1983
WO 0210737 A2 2/2002

OTHER PUBLICATIONS

Brono Lebrun, Yves Jayet, Jean-Claude Baboux; "Pulsed eddy current signal analysis: application to the experimental detection and characterization;" 1997; NDT&E International; vol. 30, No. 3; pp. 163-170.*
(Continued)

*Primary Examiner* — Mischita Henson
*Assistant Examiner* — Christine Liao

(57) ABSTRACT

In a general methodology for insulation defect identification in a generator core, a Chattock coil is used to measure magnetic potential difference between teeth. Physical knowledge and empirical knowledge is combined in a model to predict insulation damage location and severity. Measure-
(Continued)

ments are taken at multiple excitation frequencies to solve for multiple characteristics of the defect.

19 Claims, 12 Drawing Sheets

(51) Int. Cl.
    *G06F 17/11*     (2006.01)
    *G01R 31/34*     (2006.01)
    *G01N 27/20*     (2006.01)
    *G01R 31/12*     (2006.01)

(52) U.S. Cl.
    CPC .......... *G01N 27/82* (2013.01); *G01R 31/1227* (2013.01)

(58) Field of Classification Search
    USPC ............................................ 324/242; 702/38
    See application file for complete search history.

(56) References Cited

U.S. PATENT DOCUMENTS

| | | | |
|---|---|---|---|
| 5,990,688 | A | 11/1999 | Bourgeois et al. |
| 6,469,504 | B1* | 10/2002 | Kliman et al. ................ 324/228 |
| 7,385,392 | B2* | 6/2008 | Schlicker ............... G01N 27/82 324/242 |
| 2003/0117144 | A1* | 6/2003 | Sutton .......................... 324/546 |
| 2004/0000923 | A1 | 1/2004 | Fischer et al. |
| 2006/0033504 | A1* | 2/2006 | Barber et al. ................. 324/523 |
| 2007/0250277 | A1* | 10/2007 | Hagit et al. ..................... 702/64 |

OTHER PUBLICATIONS

G. Klempner; Ontario Hydro "Experience and Benefit of Using EL-CID for Turbine-Generators" Electric Power Research Institute Motor & Generator Predictive Maintenance & Refurbishment Conference; Orlando, Florida; Nov. 28-30, 1995.
International Search Report dated Apr. 26, 2013.
de la Barrera et al., "Experimental generation and quantification of stator core faults on induction motors" in: Diagnostics for Electric Machines, Power Electronics and Drives, 2009. SDEMPED 2009. IEEE International Symposium on, IEEE, pp. 1-7.
Bates et al., 2004. "Formulation of the optimal Latin hypercube design of experiments using a permutation genetic algorithm", AIAA 2004-2011 , 1-7.
Chattock, A., 1887. "On a magnetic potentiometer". Proceedings of the physical society of London 9, 23.
Ghate et al, 2010. "Optimal mlp neural network classifier for fault detection of three phase induction motor". Expert Systems with Applications 37, 3468-3481.
Grubic et al., 2008. "A survey on testing and monitoring methods for stator insulation systems of low-voltage induction machines focusing on turn insulation problems". Industrial Electronics, IEEE Transactions, vol. 55, No. 12, Dec. 2008, pp. 4127-4136.

Han et al, 1993. "Data-driven discovery of quantitative rules in relational databases". Knowledge and Data Engineering, IEEE Transactions, vol. 5, No. 1, Feb. 1993, pp. 29-40.
Haq et al., 2008. "Insulation Problems in Medium-Voltage Stator Coils Under Fast Repetitive Voltage Pulses". Industry Applications, IEEE Transactions on 44, 1004-1012.
Iman et al, 1981. "An approach to sensitivity analysis of computer models. I—Introduction, input, variable selection and preliminary variable assessment". Journal of Quality Technology, vol. 13, No. 3, Jul. 1981, pp. 174-183.
Iman et al, 1982. "Sensitivity Analysis Techniques: Self Teaching Curriculum". The Commission.
Iman et al., 1985. "Comparison of uncertainty and sensitivity analysis techniques for computer models". Technical Report. Sandia National Labs., Albuquerque, NM (USA).
Kuo, 2010. "Artificial identification system for transformer insulation aging". Expert Systems with Applications 37, 4190-4197.
McKay et al, 1979. "A comparison of three methods for selecting values of input variables in the analysis of output from a computer code". Technometrics 21, 239-245.
McNamara, 2000. "Electromagnetic Core Imperfection Detection (ELCID)". Latin America Power 2000, Caracas, Venezuela, May 15, 2000.
Myers et al, 1971. "Response surface methodology". Allyn and Bacon Boston.
Paley et al, 1998. "Verification of the effectiveness of EL CID on a hydrogenerator stator core", in: Hydrovision Conference.
Paley, 1999. "Current low power core testing using EL CID", in: Understanding your Condition Monitoring (Ref. No. 1999/117), IEE Colloquium on, IET. pp. 7/1-7/4.
Rickson, 1986. "Electrical machine core imperfection detection". Electric Power Applications, IEE Proceedings, vol. 133, Pt. B, No. 3, May 1986, 190-195.
Sathiyasekar et al, 2011. "Neuro fuzzy based predict the insulation quality of high voltage rotating machine". Expert Systems with Applications 38, 1066-1072.
Sutton, 1994. "Theory of electromagnetic testing of laminated stator cores". Insight, vol. 36, No. 4, Apr. 1994, pp. 246-251.
Tallam et al., 2007. "A survey of methods for detection of stator-related faults in induction machines". Industry Applications, IEEE Transactions, vol. 43, No. 4, Jul./Aug. 2007, pp. 920-933.
Tumanski, 2007. "Induction coil sensorsa review". Measurement Science and Technology 18, R31.
Widodo, 2007. "Combination of independent component analysis and support vector machines for intelligent faults diagnosis of induction motors". Expert Systems with Applications 32, 299-312.
Wyss et al, 1998. "A user's guide to LHS: Sandia's Latin hypercube sampling software". SAND98-0210.
Canadian Report of Examination mailed Dec. 16, 2015 (4-pages).
Korean Report of Examination mailed Mar. 17, 2015 corresponding to KoreanApplication No. 10-2014-7020552 filed Jan. 13, 2013 3 (27 pages).
Paley, D.B. et al; "Low Power Stator Core Fault Testing Using EL CID"; Power system technology; Powercon 1998; International conference on Beijing pp. 1010-1014; XP010312727; ISBN: 0-7803-4754-4; 1998.

* cited by examiner

INSULATION DEFECT DETECTION OF HIGH VOLTAGE GENERATOR STATOR CORE

CLAIM OF PRIORITY

This application claims priority to, and incorporates by reference herein in its entirety, U.S. Provisional Patent Application Ser. No. 61/589,425, filed Jan. 23, 2012, and entitled "Insulation Defect Detection of High Voltage Generator Stator Core."

FIELD OF THE INVENTION

This invention relates generally to techniques for detecting insulation defects in electrical generator cores. More particularly, the invention relates to using measurements of magnetic potential difference between core teeth in predicting the location and severity of the defect.

BACKGROUND OF THE INVENTION

Insulation failure is one of the major failure modes in high voltage generator cores. Mechanical and thermal stresses may degrade the insulation quality and cause the initiation of a minor defect. A minor insulation defect can develop into a severe defect because of localized thermal and electrical stresses generated by the defect-induced current. The combination of these stresses causes time-dependent degradation of the insulation.

Due to the high reliability-demanding nature of generators, insulation defects must be identified at an early stage in order to avoid catastrophic events, and to reduce operation and maintenance costs during the lifecycle of the generator. Effective and efficient insulation defect detection methods have therefore become a practical requirement in the modern power generation field. Although considerable research efforts have been made in this topic since the early 1980s, the detection of defects while minimizing generator downtime is a complex engineering task that involves many fields of knowledge. It is not a trivial task for ordinary engineers without expertise to successfully perform reliable defect identifications.

SUMMARY OF THE INVENTION

The present invention addresses the needs described above by providing a method for detecting an insulation defect in a generator core. The method includes flowing an alternating excitation current at a first excitation frequency through an excitation winding adjacent the generator core to induce first eddy currents between laminations at the defect; and measuring a first potentiometer voltage indicating magnetic flux caused by the first eddy currents induced at the first excitation frequency.

An alternating excitation current at a second excitation frequency is then flowed through the excitation winding adjacent the generator core to induce second eddy currents between the laminations at the defect, and a second potentiometer voltage indicating magnetic flux caused by the second eddy currents induced at the second excitation frequency is measured.

A severity of the defect and a depth of the defect are determined using a semi-empirical relationship between the potentiometer voltages, the excitation frequencies, the severity of the defect and the depth of the defect.

In another aspect of the invention, a non-transitory computer-usable medium is provided having computer readable instructions stored thereon for execution by a processor to perform methods for detecting an insulation defect in a generator core as described above.

DESCRIPTION OF THE INVENTION

Figure 1A:
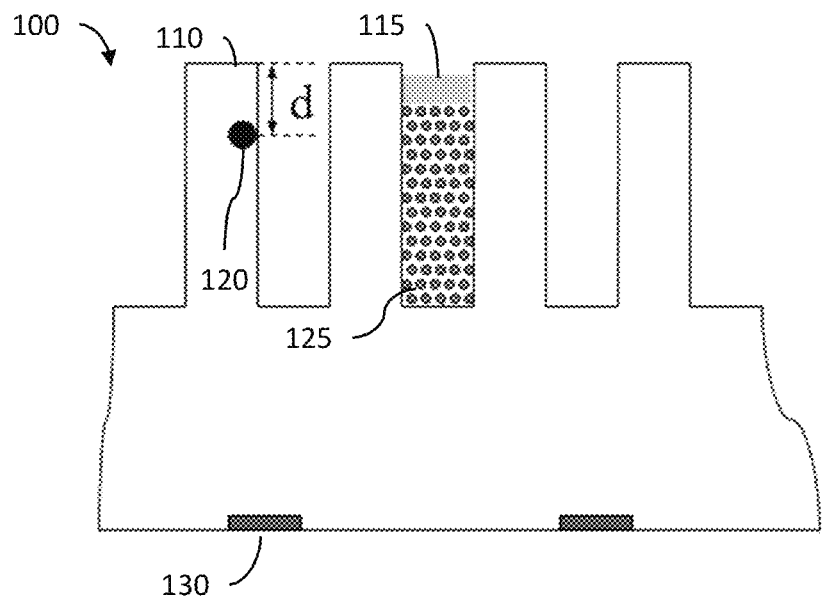
FIG. 1A is a schematic cross sectional representation of a stator core with an insulation defect of a type detected by the methods of the invention.

Insulation defect detection in a generator stator core using thermal distribution and a magnetic field variation introduced by the defects has drawn extensive attention in industry over the past decades. In practice, a large number of failure mechanisms causing insulation defects exist due to factors such as insulation materials, design practices, operation environments, geometry configurations, and so on. Interpreting test results is therefore a highly nontrivial task. To implement such a task, many fields such as electrical engineering, material science, structure engineering, and mechanical engineering are involved and field-specific expertise is generally required. Many of the reported studies involving expert systems are generally data-driven methods, and do not consider the fundamental governing physics. Data-driven methods can produce satisfactory results given sufficient training data and a relatively stationary degradation mechanism. Without considering fundamental underlying physics, however, there is increased difficulty in explaining prediction results. Obtaining the required training data in industrial generators is very time-consuming and expensive. Therefore, incorporating the fundamental physics can improve the robustness of the expert system constructed using limited data.

In the present disclosure, an expert system is developed for generator motor insulation defect detection and quantification. An Electromagnetic Core Imperfection Detector (ELCID) test is preformed to scan the stator core to obtain the magnetic field data around the core. Fundamental physical laws and expert knowledge are combined to form an expert system to predict locations and severity of insulation defects. The expert system is implemented as an analysis software system to help field personnel perform rapid diagnostics and prognostics of the generator stator core.

The expert system of the present disclosure is a model for damage identification and severity prediction in which a semi-empirical physical theory model is integrated. The expert system provides a platform for data import and visualization, and damage identification and severity prediction.

Electromagnetic Core Imperfection Detector (ELCID) Test

Traditionally, stator cores of large motors and generators have been tested for hot spots. That approach uses an external excitation winding to produce a circumferential electromagnetic ring flux around the core. The insulation defect and other components in stator cores, such as building bars or key bars, will produce an induced circulating current. The resulting localized heat can increase the temperature around the defect. Once the temperature distribution of the stator core is stable, an infrared camera scans along and around the bore surface and measures the temperatures of the tips of the stator teeth. Surface insulation defects can be relatively easy to detect using that technique, but it is usually difficult to detect deep seated defects and those below the coil windings. Another drawback of this approach is that it can potentially damage the stator. Testing a large core using the hot spots approach would typically require several turns of 11 kV cable capable of carrying approximately 300 A current. Because the defect-induced current is approximately proportional to the electromagnetic flux generated by the excitation current, producing a significant temperature rise requires 80% of the normal operating flux density in the core. For example, using this approach to perform a testing for a 500 MW generator would require an excitation winding connected to a supply on the order of 3 MVA. In case of shorts between the laminations, the induced current can produce serious overheating and damage the winding or deteriorate a minor insulation defect.

The Electromagnetic Core Imperfection Detector (ELCID) test is another widely accepted approach in industry for detecting generator core insulation defects. It overcomes the power requirement of the hot spots approach, and requires only 4% of the normal operating flux. The basic idea is to sense the magnetic field resulting from the fault current induced by the insulation defect. A Chattock potentiometer applied across the teeth of the stator core can be used to detect the magnetic field. The response of the ELCID test includes a quadrature trace (QUAD) and a phase trace (PHASE). In general, the value of the QUAD trace is proportional to the fault current induced by the insulation defect, and the value of the PHASE trace is proportional to the excitation current. By inspecting the QUAD trace, insulation defects can be identified.

Components of ELCID Test

Figure 1B:
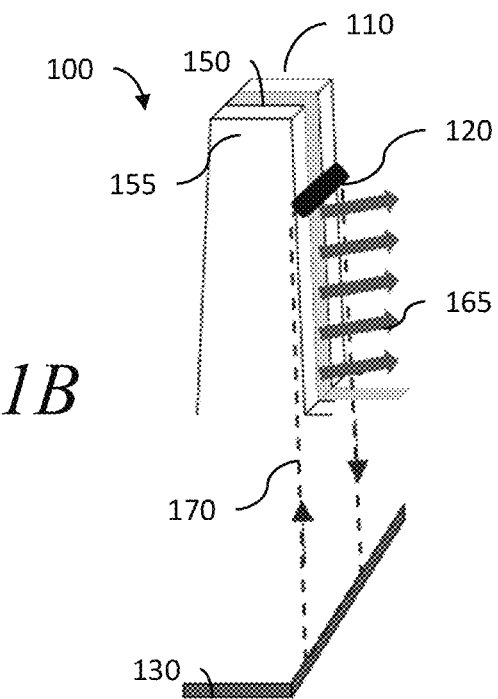
FIG. 1B is a schematic view of a stator core tooth with an insulation defect of a type detected by the methods of the invention.

The stator cores of a generator stator 100, shown in FIGS. 1A and 1B, are built of laminations 155 of magnetic steel. A thin layer of electrical insulation 150 prevents currents from flowing between these laminations. All the laminations are connected with metallic key bars 130, as shown in FIGS. 1A, 1B. If the insulation 150 between laminations 155 is damaged, causing a defect 120, the alternating magnetic flux 165 through the stator core 100 can generate eddy currents 170 flowing between the laminations.

Figure 2:
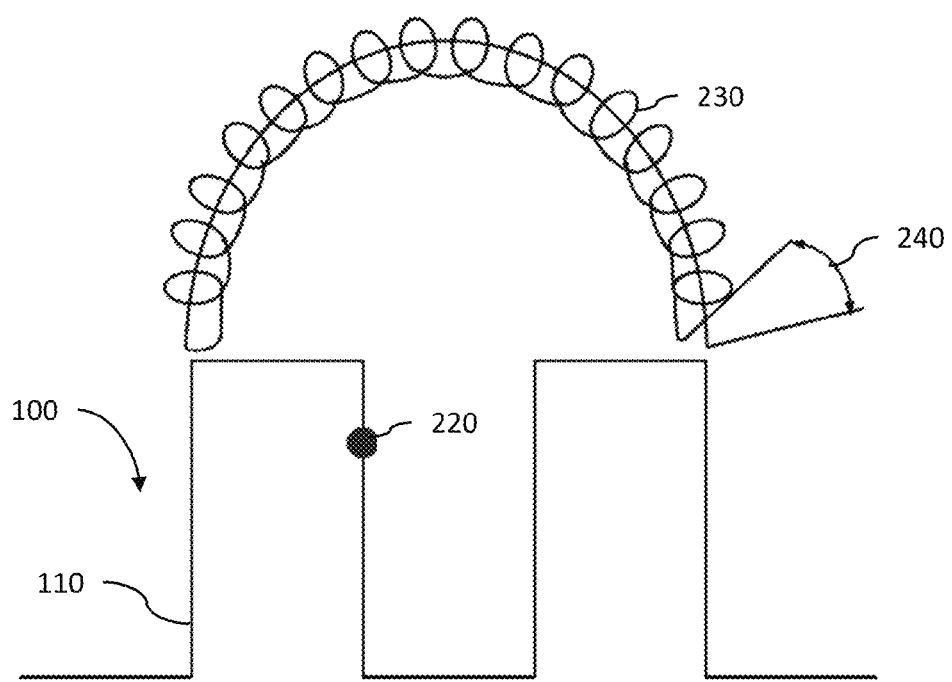
FIG. 2 is a schematic representation of Chattock potentiometer in use according to one embodiment of the invention.

The eddy currents 170 induced in any areas can be detected using a Chattock potentiometer 230, shown in FIG. 2, applied across the teeth 110 of the stator core having a current 220 flowing along the iron surface of the teeth. The Chattock potentiometer 230 comprises of a uniform air-cored coil, which measures the magnetic potential difference (MPD) between its ends. The voltage measurement 240 is generally proportional to the fault current. The span of the coil is adjusted to just bridge between furthest corners of adjacent teeth 110. An excitation winding (not shown) produces a large MPD between teeth. Because the permeability is approximately constant around the stator core 100, the flux from the excitation winding is uniformly distributed around the core. The MPD between teeth not carrying defect-induced currents can be expressed as $I_w/N$, where $I_w$ (in Ampere turns) is the excitation winding current and N is the number of the teeth 110 of the stator core 100. For instance, for a 48 tooth stator core with a typical 50 A turns excitation winding, the MPD between adjacent teeth is 50/48≈1 A.

The Chattock potentiometer measures the MPD due to both the fault current and the excitation current. It is common that the excitation winding MPD, for example, 1 A between adjacent teeth, is larger than the defect induced current. To measure the defect induced current, the excitation winding induced current must be removed. That is achieved by using a phase sensitive detector to measure the component of MPD in quadrature with the excitation current. The instantaneous excitation current is $I_w = \sqrt{2} I_w \sin \omega t$, where ω is the excitation frequency and t is a time index. For a surface short defect, the instantaneous defect induced current through the damaged region is $$i_F = \frac{l_F}{l_C}\sqrt{2}\, V_w \frac{R_F \cos\omega t + \omega L_F \sin\omega t}{R_F^2 + (\omega L_F)^2}$$

where $R_F$, $L_F$, and $l_F$ are the resistance, inductance and length of the defect induced current 170, respectively, and $l_C$ and $V_w$ are the length of the core 100 and the root mean square (RMS) voltage induced in a single turn winding around the core. Given that the inductance of the defect circuit is much lower than its resistance, i.e., $\omega L_F \ll R_F$, the above equation may be approximated using the following:

$$i_F \approx \frac{l_F}{l_C} \frac{\sqrt{2}\, V_w \cos\omega t}{R_F}.$$

Comparing with the excitation current $i_w = \sqrt{2} I_w \sin\omega t$, the defect induced current $i_F$ in the above equation is in phase quadrature with $i_w$, and therefore can readily be measured using a phase sensitive detector. Actual ELCID test devices have two output traces. One is the PHASE trace corresponding to the excitation current and another one is the QUAD trace corresponding to the defect induced current. According to the above equation, the RMS value of the defect induced current can approximately be expressed as $$i_F \approx \frac{l_F}{l_C} \frac{V_w}{R_F}.$$

This equation indicates that the defect induced current is proportional to the excitation winding voltage $V_w$ and the defect current length $l_F$ and is inversely proportional to the resistance $R_F$ of the defect circuit.

Basic Theory of ELCID Test

The basic theory of ELCID operation is based on Ampere's law, which states that for any closed loop of the line integral, the magnetic intensity is equal to the enclosed current I. Ampere's law is expressed as $$\oint H \cdot dl = I,$$

where H is the electromagnetic flux. If the current 220 flows along an iron surface, as shown in FIG. 2, the equation can be expressed as $$\oint H \cdot dl = \int_{air} H \cdot dl + \int_{iron} H \cdot dl = I.$$

Since the permeability of the iron is much larger compared with that of the air, the field (magnetic field strength H) in the iron is much less than that in the air. Therefore, the current component associated with iron is negligible and the above equation is reduced to $$\int_{air} H \cdot dl \approx I.$$

A Chattock potentiometer measures the difference in magnetic scalar potential between its two ends. The output voltage due to the current is given by $$V = \mu_0 \omega n A I.$$

Terms $\mu_0$, $\omega$, n, and A are the permeability of free space, the angular frequency of the excitation current, the number of turns per meter of the winding, and the cross section area of the winding, respectively. That equation indicates the coil sensitivity or output value is independent of its length and its path in air. The current I comprises two components: the fault current induced by the insulation defect and the excitation current. In practice, the excitation current (the measured PHASE trace of the ELCID test) is removed by a compensation coil. The resulting voltage measurement can be safely expressed as $$V \propto \mu_0 \omega n A I_F.$$

Substitute the above approximation of $I_F$ into the above equation to obtain $$V \propto \omega \frac{l_F}{R_F} \frac{V_w}{l_C} \mu_0 n A.$$

The ultimate goal of the ELCID test is not only to identify the existence of the insulation defect, but also to locate the actual position and severity of the defect for timely and economic maintenance operation. The depth information is of great importance for field repair because a surface insulation defect is much easier to fix than a deeply seated defect. Knowledge of the depth of a detectable defect can therefore greatly facilitate practical maintenance work. The response voltage V in the above equation is derived from the surface short defect. For a defect that is located beneath the surface, the equation must be modified by introducing a depth parameter d, as shown in FIG. 1A. The variable d measures the distance from the tooth tip to the location of the defect-induced current. Next, a new voltage response involving the depth parameter d is developed based on semi-empirical modeling.

Figure 3:
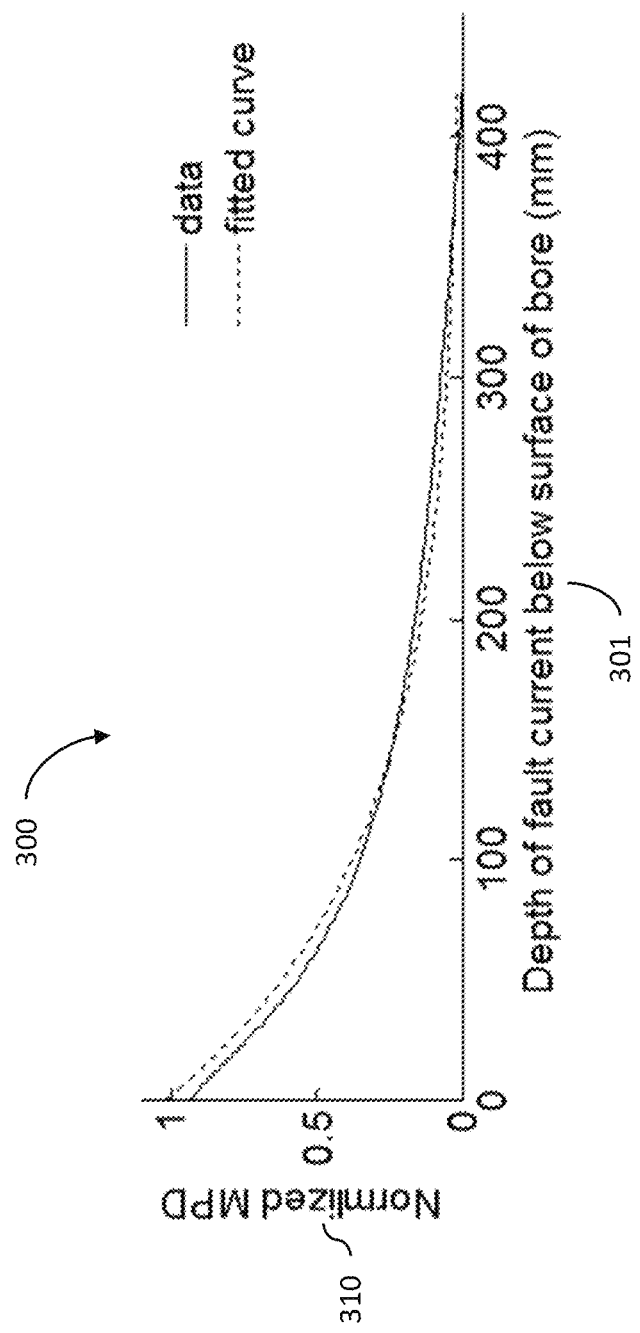
FIG. 3 is a graph showing a relationship between a normalized magnetic potential difference, and a depth of an insulation fault current, together with a fitted curve, in accordance with one embodiment of the invention.

Measurement Response Modeling and Parameter Estimation: A Physics Model Based on Semi-Empirical Modeling The underlying physics that causes the voltage response to vary is a multi-mechanism. For example, the geometry of the defect, the location of the defect, the thickness of the lamination and insulation and many other factors can affect the response. In addition, device calibration, measurement, and the phase sensitive compensation coil can introduce uncertainties to the response. To parameterize the model to consider major influence factors, several assumptions are made in the present disclosure based on empirical modeling of the experimental data. One assumption is that the defect induced current has an exponential attenuation function involving the depth parameter d. Based on a data analysis reported by Sutton, J., Theory of electromagnetic testing of laminated stator cores, Insight 36, 246-251 (1994), which is incorporated herein by reference in its entirety, an assumption is made that the MPD induced by the defect can be modeled using an exponential decay function under a specific frequency. Sutton's data 300, summarized in FIG. 3 of the present disclosure, illustrates the exponential variation of the normalized MPD 310 with respect to the depth of the defect induced current 301.

Using that assumption, the following relationship can be derived from the above equation defining the response voltage V:

$$V \propto \omega \frac{l_F}{R_F} \exp\{-\alpha d\omega\} \frac{V_w}{l_C} \mu_0 n A$$

where $\alpha$ is the attenuation coefficient, d is the depth of the defect, and $\omega$ is the excitation frequency.

Since the term $$\frac{V_w}{I_C}$$

Figures 4A, 4B:
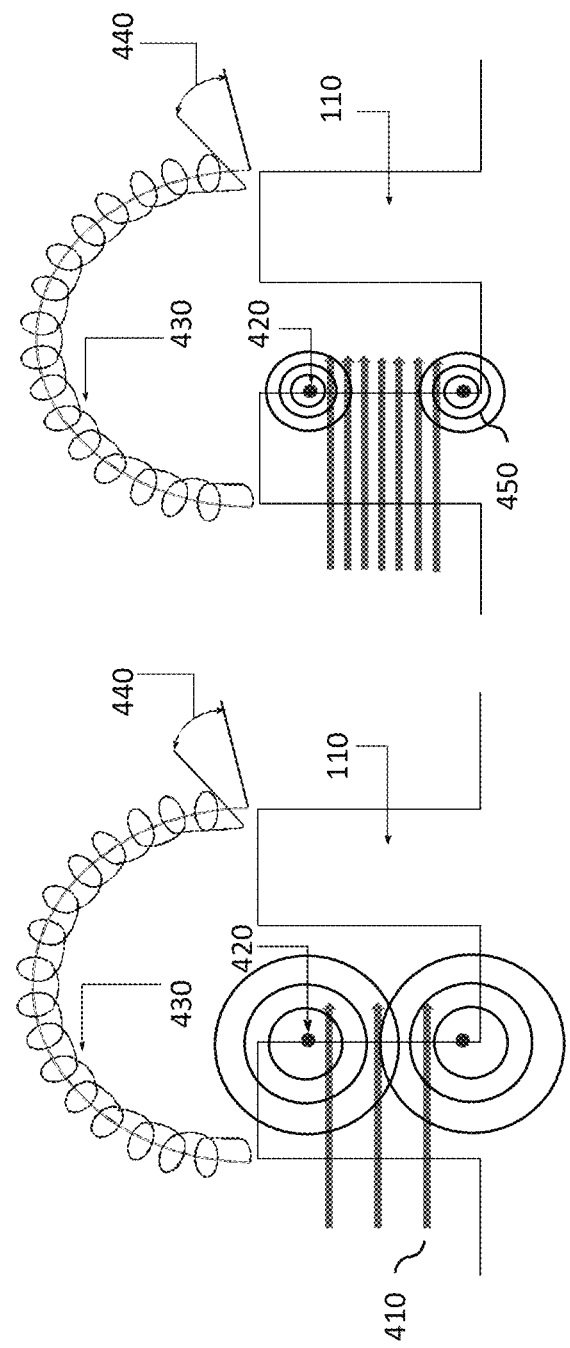
FIG. 4A is a schematic representation of a potentiometer measurement, illustrating an assumption made in accordance with one embodiment of the invention.
FIG. 4B is a schematic representation of a potentiometer measurement, illustrating another assumption made in accordance with one embodiment of the invention.

$\mu_0 nA$ is related to the potentiometer and is a constant for a specific testing device, the term $$\frac{l_F}{R_F}$$

can be used to characterize the severity s of the defect (damage level). Two additional assumptions are made about the mechanism by which the response voltage 440 is produced by the Chattock potentiometer 430, as shown in FIGS. 4A and 4B. First, as illustrated in FIG. 4A, it is assumed that the magnetic flux 410 produced by current 420 on a tooth 110 is uniformly distributed across the core. Second, as shown in FIG. 4B, it is assumed that a higher frequency magnetic field 450 has a higher attenuation coefficient value. Therefore, the above equation can be safely expressed as $$V = k s \omega^{1+\beta} \exp[\alpha d \ln \omega]$$

where $\alpha$, $\beta$ and k are three fitting parameters. The term $$s = \frac{l_F}{R_F}$$

is the severity of the defect. The three fitting parameters $\alpha$, $\beta$ and k should be estimated from ELCID test data.

Measurement Response Modeling and Parameter Estimation: A Data-Driven Model Based on Response Surface Method A data-driven model can alternatively be developed. A response surface method described in Myers, R. et al., Response surface methodology (Allyn and Bacon Boston 1971), which is incorporated herein by reference in its entirety, is employed in this disclosure to develop a data-driven model. Two variables, the depth d and the severity s, are of interest. For illustration purposes, a second order response surface model g is used to construct the relationship between the measurable voltage V and the (d, s). For a given excitation frequency $\omega$, the model is expressed as $$g(d,s|\omega) = p_{00} + p_{10}d + p_{01}s + p_{11}ds + p_{20}d^2 + p_{02}s^2$$

where $p_{ij}$ with i,j=0, . . . , 2 are model parameters. One skilled in the art will realize that other models may be used.

Design of Experiments Methodology Using Latin Hypercube Sampling

Latin hypercube sampling (LHS) is a statistical method for generating a distribution of plausible collections of parameter values from a multi-dimensional distribution. It is often used in design optimization for two main reasons: (1) to minimize the number of response evaluations and required experimental tests, and (2) to reduce the effect of numerical noise. For the completeness of this study, the basic idea is described here.

Latin hypercube sampling is a constrained Monte Carlo sampling in nature. Latin hypercube sampling selects N different values from each of K variables $X_1$, . . . , $X_K$ in the following manner. The range of each variable is divided into N non-overlapping intervals on the basis of equal probability. One value from each interval is selected at random with respect to the probability density in the interval. The N values thus obtained for $X_1$ are paired in a random manner (equally likely combinations) with the N values of $X_2$. These N pairs are combined in a random manner with the N values of $X_3$ to form N triplets, and so on, until N K-tuplets are formed.

Many statistical packages provide a realization of the LHS method. One such statistical package is Matlab® lhsdesign function.

One significant merit of the LHS is that design of experiments (DoE) results of LHS are independent of the model and application. Once the DoE for K variables and N points is formulated, re-calculation of the DoE is not required when different models are used.

To obtain a DoE scheme for the ELCID testing, both variables s and d are divided into four levels. The following table presents the normalized LHS results, normalized to the range of (0,1).

| Testing No. | d | s |
| --- | --- | --- |
| 1 | 0.7984 | 0.6436 |
| 2 | 0.6945 | 0.1489 |
| 3 | 0.0001 | 0.3999 |
| 4 | 0.4841 | 0.9720 |

The results were generated in Matlab® 2010b using the function lhsdesign (4,2). To deploy the DoE for field testing, the depth and size should be quantified first. For example, given the total length of the tooth L and the defect size range 0~10, the testing No. 1 (0.7984, 0.6436) corresponds to the actual depth of 0.7984×L and an actual defect size of 0.6436×10≈6.4. Other testing combinations in this table follow the same procedure to convert normalized values to actual testing values.

In practice, a defect with a precise size configuration is difficult to artifact and measure. One known means to artifact the defect is to use screws. Taking the defect size of 6.4 (≈6) as an example, 6 screws can be inserted into the depth of 0.7984 L≈0.8 L to represent this testing combination. Solders and lengths of copper wire are also used to emulate shorts.

ELCID Tests for Parameter Estimation

Several ELCID tests are conducted with artificial defects to estimate model parameters. Several sets of experiments are performed to study the response for defects under different excitation frequencies. Artificial shorts are created between laminations using solders to represent actual insulation failures. In the first two sets of experiments, seven excitation frequencies are used (50 Hz, 60 Hz, 250 Hz, 500 Hz, 1 KHz, 2 KHz, 5 KHz).

Case 1: Responses Vs. Depth of the Defect d

Figure 5A:
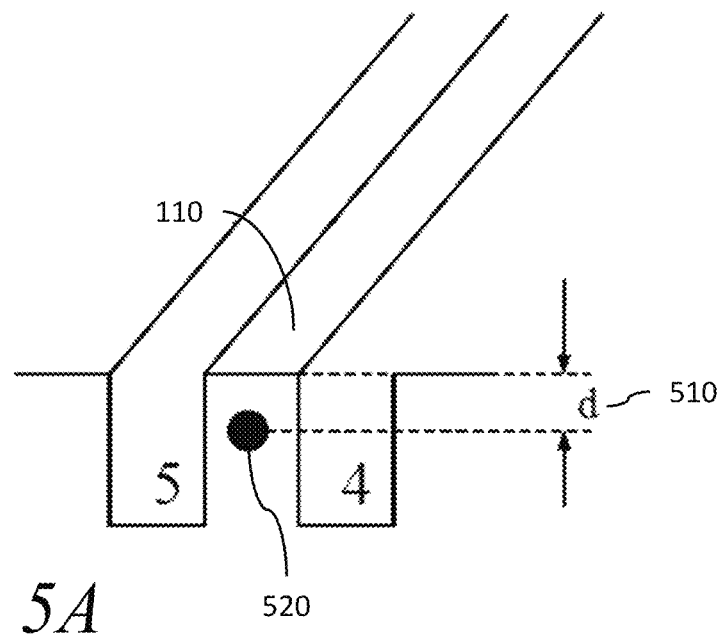
FIG. 5A is a schematic representation of a core tooth showing a depth of an artificial insulation defect, in accordance with one embodiment of the invention.
Figure 6A:
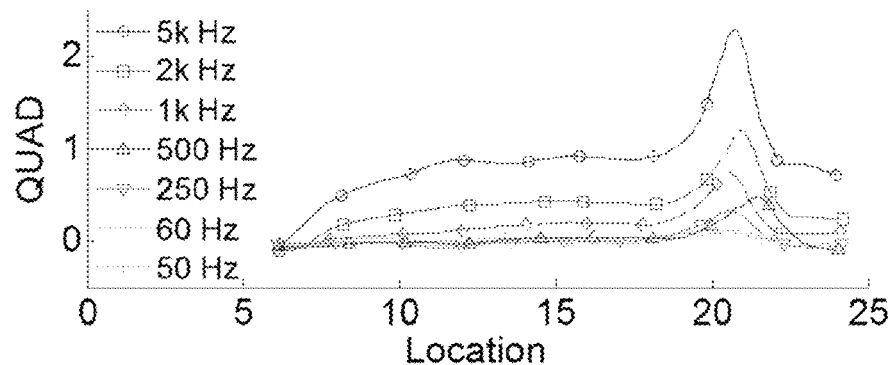
FIGS. 6A, 6B and 6C are graphs of QUAD traces for varying locations and excitation frequencies, each graph being at a different defect depth, in accordance with one embodiment of the invention.
Figure 6B:
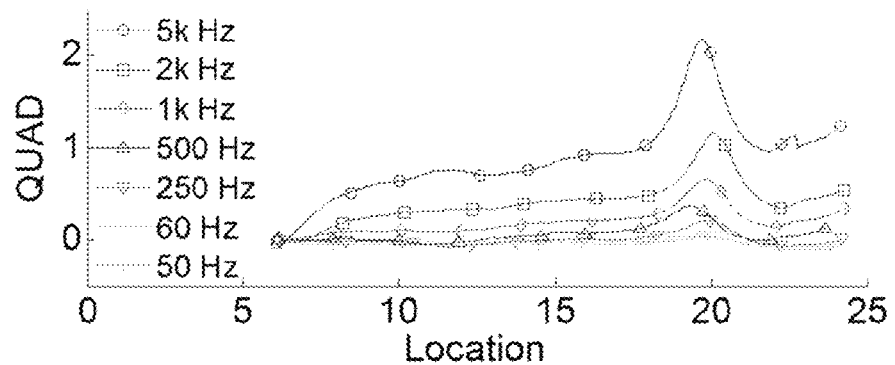
Figure 6C:
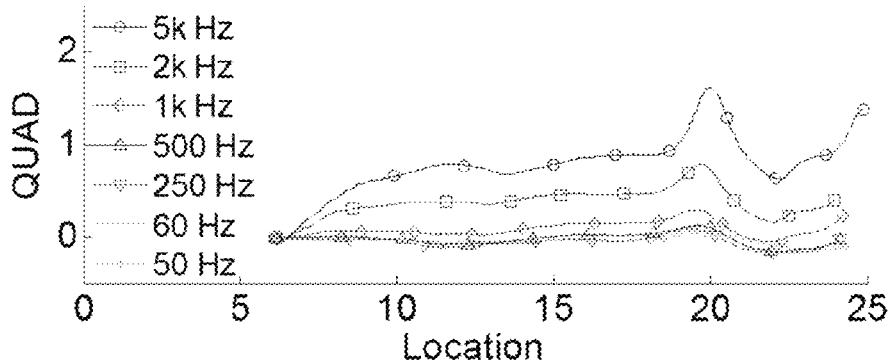

Three sets of experiments were carried out on a retired generator rotor core. As shown in FIG. 5A, artificial shorts 520 were created using solders within a tooth 110 (shown between windings 4 and 5). Three different depth configurations 510, namely, d=2.0 in, 6.0 in, and 10.0 in, were investigated using the ELCID test. QUAD trace results using multiple excitation frequencies are shown in FIGS. 6A-6C. FIG. 6A illustrates a trace using a defect depth d=2 in.; FIG. 6B illustrates a trace using a defect depth d=6 in.; and FIG. 6C illustrates a trace using a defect depth d=10 in.

Case 2: Responses Vs. Severity of the Defect s

Figure 5B:
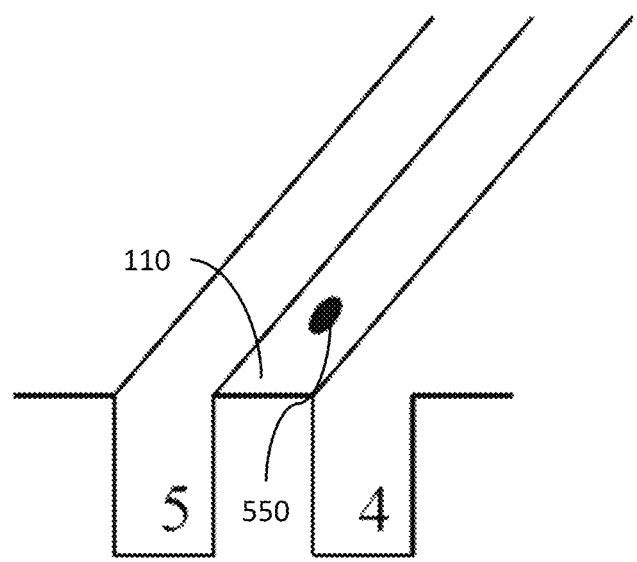
FIG. 5B is a schematic representation of a core tooth showing a severity of an artificial insulation defect, in accordance with one embodiment of the invention.
Figure 7A:
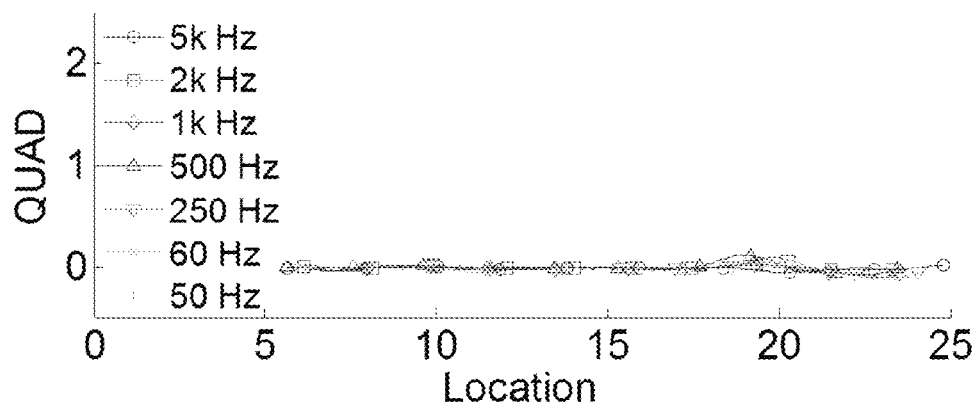
FIGS. 7A and 7B are graphs of QUAD traces for varying locations and excitation frequencies, each graph being at a different defect severity, in accordance with one embodiment of the invention.
Figure 7B:
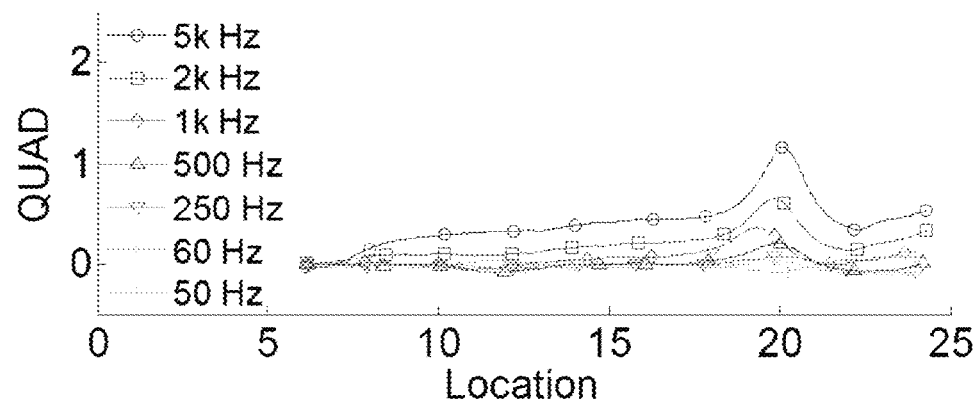

Two sets of experiments were carried out in this case. To create different damage levels, one of the experiments uses a smaller amount of solder for the defect. For illustration purposes, the defect created with a normal amount of solder corresponds to a severity quantity of s=1.0 and the defect with less solders is considered as s=0. The experimental configuration is shown in FIG. 5B, wherein defects 550 of varying severity are introduced to the tooth 110. Results of the two experiments using different excitation frequencies and QUAD traces are shown in FIGS. 7A and 7B. FIG. 7A shows traces for severity level s=0; FIG. 7B shows traces for severity level s=1.

Figure 8A:
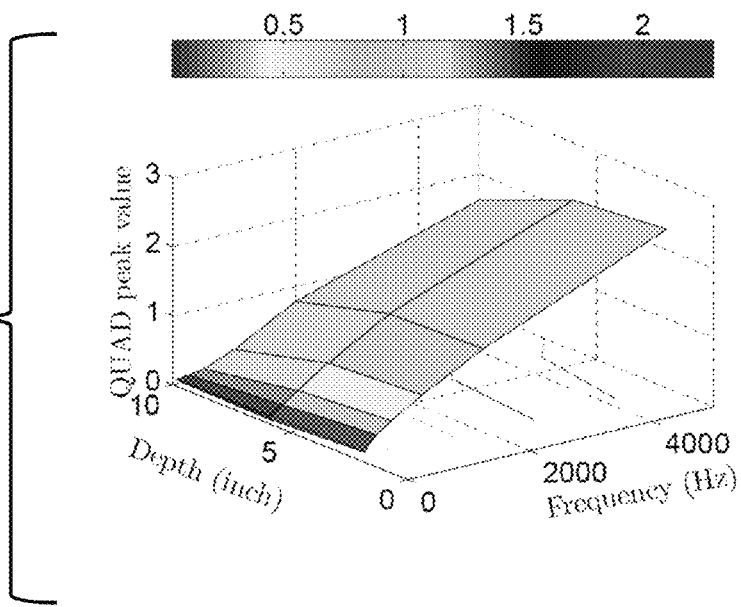
FIG. 8A is a graph of a response surface for QUAD peak values for varying excitation frequencies and varying defect depths, in accordance with one embodiment of the invention.
Figure 8B:
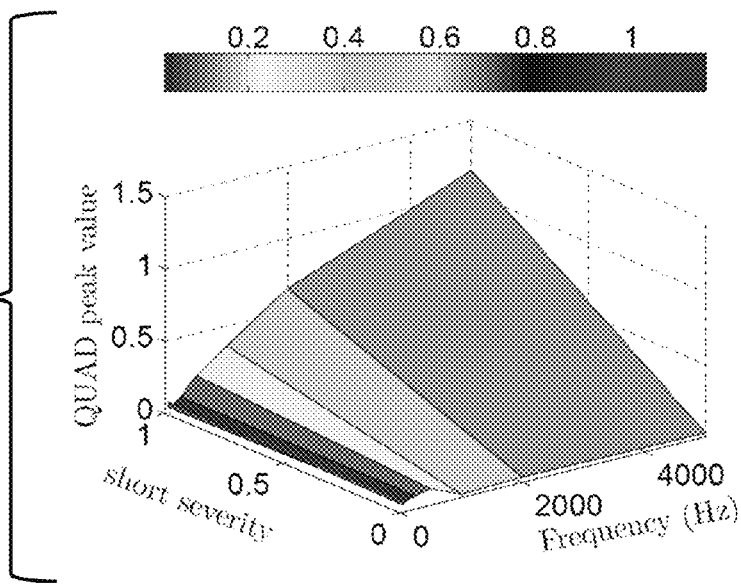
FIG. 8B is a graph of a response surface for QUAD peak values for varying excitation frequencies and varying defect severities, in accordance with one embodiment of the invention.

The x-axis in FIGS. 6 and 7 reflects the location of the damage along the axial direction of the rotor core, which can be easily identified given the length of the rotor core. The depth and severity of the defect are irrelevant to the axial position of the defect. The response of the model is the peak value of the QUAD trace. Peak picking algorithms can be used to extract the peak value from the QUAD trace. FIG. 8A shows a response surface (peak value of the QUAD trace) for different defect depths. FIG. 8B shows a response surface for different defect severities.

To identify the model parameters, both probabilistic and deterministic approaches can be used. Probabilistic parameter identification instead of deterministic identification can retain much more information. The resulting probabilistic model can encode uncertainties in prediction for probabilistic analysis.

Figure 9A:
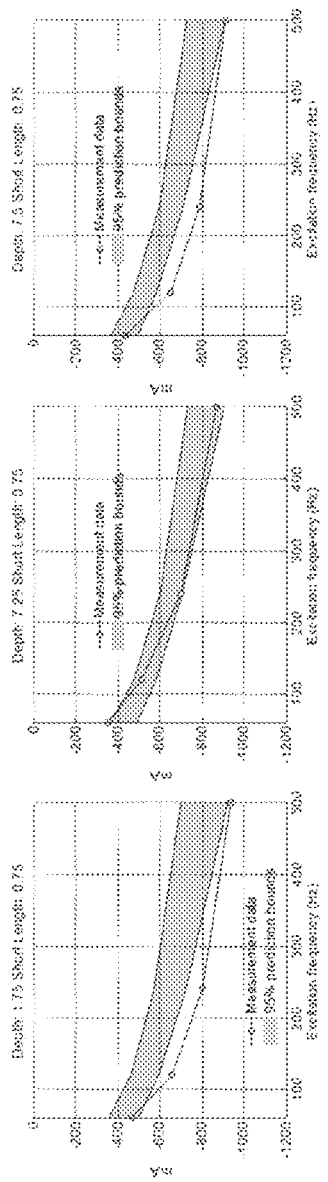
FIG. 9A shows graphs of current measurements at varying excitation frequencies, for three different defect depths, using a short length of 0.75 inches, together with a prediction by a model in accordance with one embodiment of the invention.
Figure 9B:
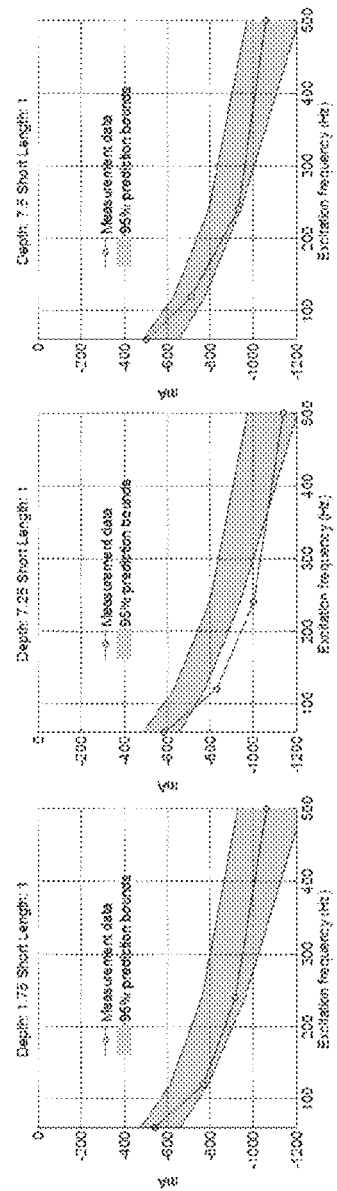
FIG. 9B shows graphs of current measurements at varying excitation frequencies, for three different defect depths, using a short length of 1.0 inch, together with a prediction by a model in accordance with one embodiment of the invention.

Additional model validation data is presented in FIGS. 9A, 9B, 10A and 10B. FIG. 9A shows three graphs of current measurements at varying excitation frequencies, for three different defect depths, using a short length of 0.75 inches, together with a measurement prediction made by a physics model with semi-empirical modeling as described above. The measurements are represented by a segments connected by small circles, while a 95% bound for the model prediction is shown as a shaded area. FIG. 9B shows data for a similar experiment using a 1.0 inch short length. In both cases, there is general agreement between the model prediction and the data.

Figure 10A:
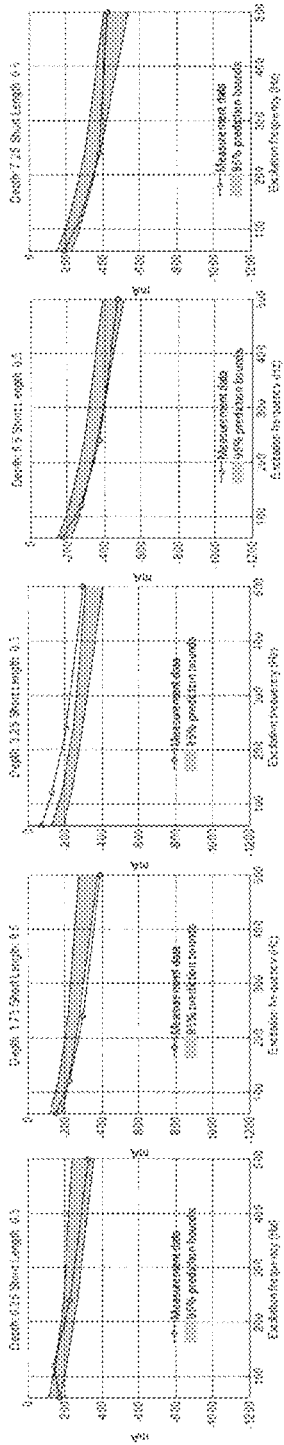
FIG. 10A shows graphs of current measurements at varying excitation frequencies, for five different defect depths in slot 4, using a short length of 0.5 inches, together with a prediction by a model in accordance with one embodiment of the invention.
Figure 10B:
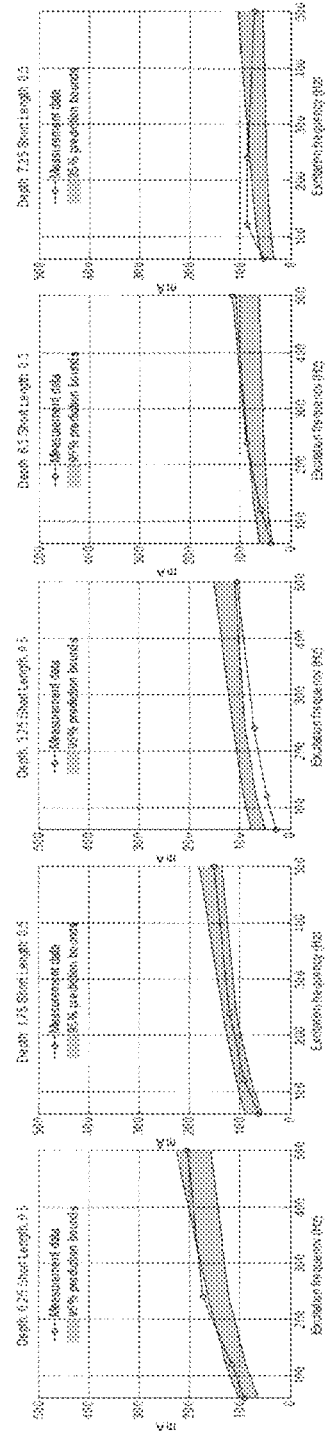
FIG. 10B shows graphs of current measurements at varying excitation frequencies, for five different defect depths in slot 5, using a short length of 0.5 inches, together with a prediction by a model in accordance with one embodiment of the invention.

FIG. 10A shows five graphs of current measurements at varying excitation frequencies, for five different defect depths in slot 4, using a short length of 0.5 inches, together with a prediction by a semi-empirical model as described above. FIG. 10B shows graphs for a similar experiment conducted with a defect located on slot 5. In each case, there is general agreement between the model prediction and the measured data.

Method

Figure 11:
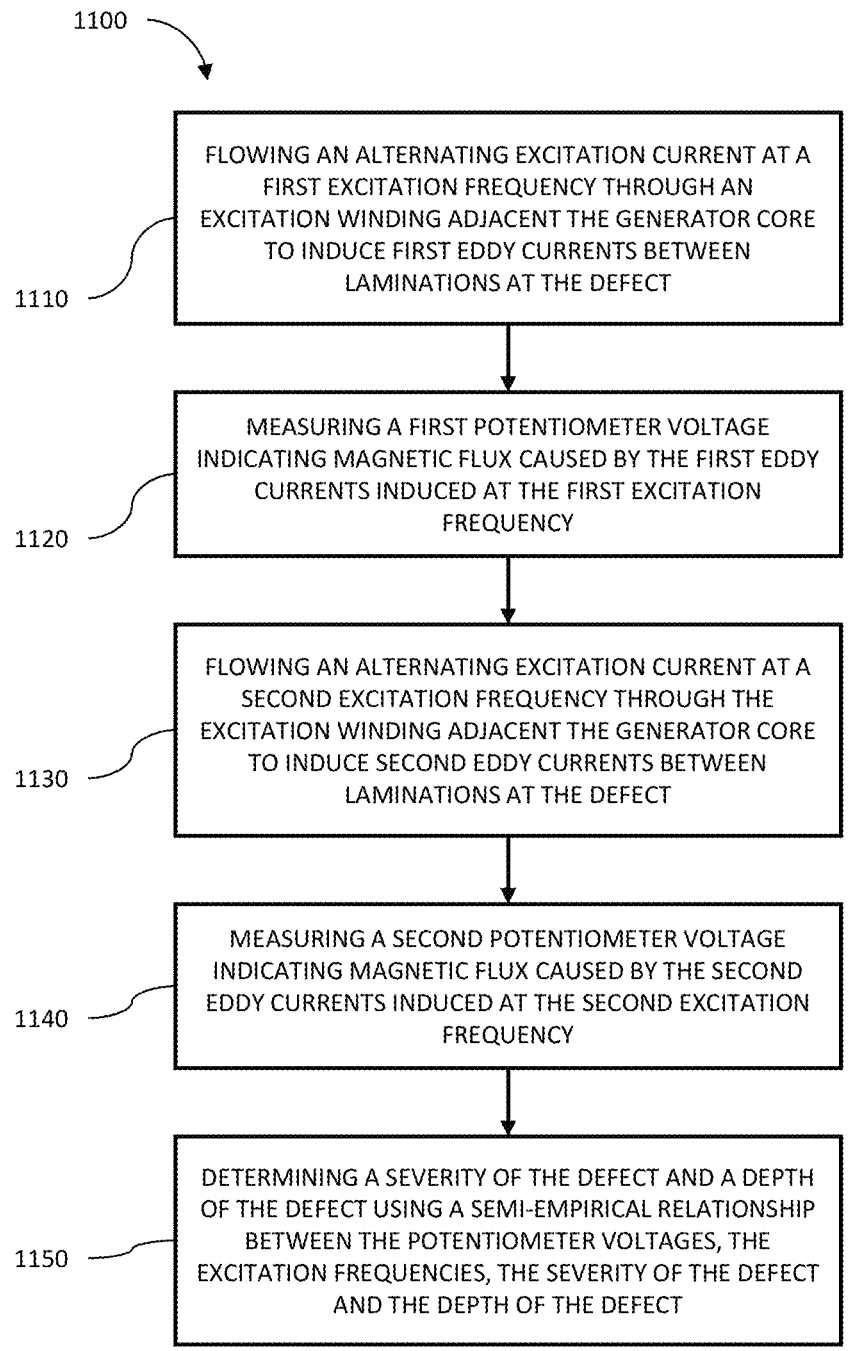
FIG. 11 is a flow chart showing a method in accordance with one embodiment of the invention.

An exemplary method for detecting an insulation defect in a generator core illustrated by the flow chart 1100 shown in FIG. 11. An alternating excitation current at a first excitation frequency is flowed at block 1110 through an excitation winding adjacent the generator core to induce first eddy currents between laminations at the defect. A first potentiometer voltage is then measured at block 1120, indicating magnetic flux caused by the first eddy currents.

An alternating excitation current at a second excitation frequency is then flowed at block 1130 through an excitation winding adjacent the generator core to induce second eddy currents between laminations at the defect. A second potentiometer voltage is then measured at block 1140, indicating magnetic flux caused by the second eddy currents. Additional measurements may be taken at additional excitation frequencies in order to increase the accuracy of the calculations or to solve for additional unknowns.

The technique determines a severity of the defect and a depth of the defect at block 1050 using a semi-empirical relationship between the potentiometer voltages, the excitation frequencies, the severity of the defect and the depth of the defect.

System

Figure 12:
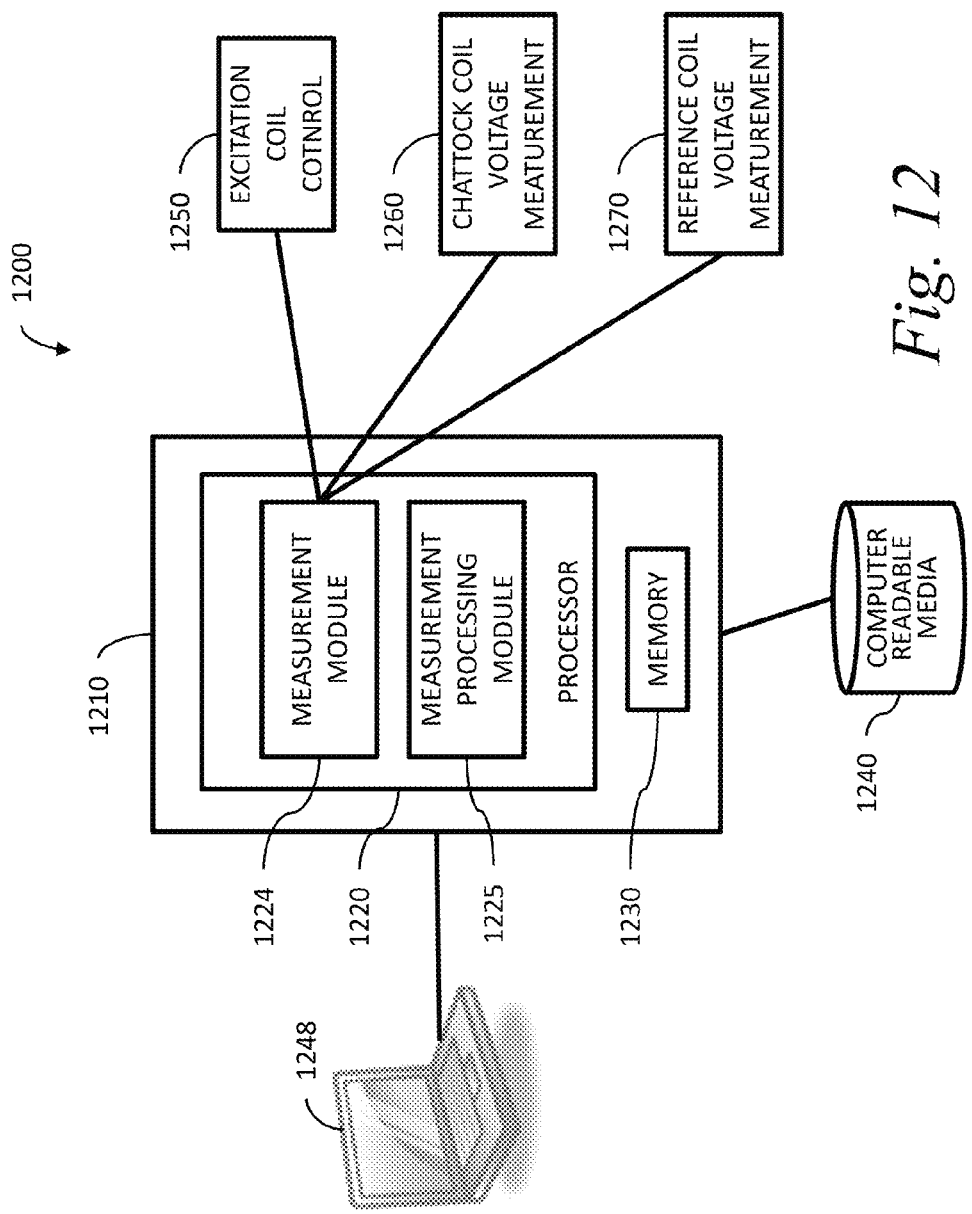
FIG. 12 is a schematic diagram showing a computer system in accordance with one embodiment of the invention.

The elements of the methodology as described above may be implemented in a computer system comprising a single unit or a plurality of units linked by a network or a bus. An exemplary system 1200 is shown in FIG. 12.

A computing apparatus 1210 may be a mainframe computer, a desktop or laptop computer or any other device or group of devices capable of processing data. The computing apparatus 1210 receives data from any number of data sources that may be connected to the apparatus. For example, the computing apparatus 1210 may receive input from a user via an input/output device 1248, such as a computer or a computing terminal. The input/output device includes an input that may be a mouse, network interface, touch screen, etc., and an output that may be a visual display screen, a printer, etc. Input/output data may be passed between the computing apparatus 1210 and the input/output device 1248 via a wide area network such as the Internet, via a local area network or via a direct bus connection. The computing apparatus 1210 may be configured to operate and display information by using, e.g., the input/output device 1248 to execute certain tasks. In one embodiment, measurements are initiated via the input/output device 1248, and measurement results are displayed to the user via the same device.

The computing apparatus 1210 includes one or more processors 1220 such as a central processing unit (CPU) and further includes a memory 1230. The processor 1220, when configured using software according to the present disclosure, includes modules that are configured for performing one or more methods for detecting an insulation defect in a generator core, as discussed herein. Those modules include a measurement module 1224 that controls an excitation coil 1250, receives measurements from a Chattock coil 1260 and measurements from a reference coil 1270, and processes those measurements to determine a coil voltage due to a magnetic potential difference caused by the defect.

The modules also include a measurement processing module 1225 that solves for a severity of the defect and a depth of the defect using a physical model of the defect and using a model of the defect based on measured data.

The memory 1230 may include a random access memory (RAM) and a read-only memory (ROM). The memory may also include removable media such as a disk drive, tape drive, memory card, etc., or a combination thereof. The RAM functions as a data memory that stores data used during execution of programs in the processor 1220; the RAM is also used as a program work area. The ROM functions as a program memory for storing a program executed in the processor 1220. The program may reside on the ROM or on any other tangible or non-volatile computer-readable media 1240 as computer readable instructions stored thereon for execution by the processor to perform the methods of the invention. The ROM may also contain data for use by the program or by other programs.

Generally, program modules 1224, 1225 described above include routines, objects, components, data structures and the like that perform particular tasks or implement particular abstract data types. The term "program" as used herein may connote a single program module or multiple program modules acting in concert. The disclosure may be implemented on a variety of types of computers, including personal computers (PCs), hand-held devices, multi-processor systems, microprocessor-based programmable consumer electronics, network PCs, mini-computers, mainframe computers and the like. The disclosed technique may also be employed in distributed computing environments, where tasks are performed by remote processing devices that are linked through a communications network. In a distributed computing environment, modules may be located in both local and remote memory storage devices.

An exemplary processing module for implementing the methodology above may be hardwired or stored in a separate memory that is read into a main memory of a processor or a plurality of processors from a computer readable medium such as a ROM or other type of hard magnetic drive, optical storage, tape or flash memory. In the case of a program stored in a memory media, execution of sequences of instructions in the module causes the processor to perform the process steps described herein. The embodiments of the present disclosure are not limited to any specific combination of hardware and software and the computer program code required to implement the foregoing can be developed by a person of ordinary skill in the art.

The term "computer-readable medium" as employed herein refers to any tangible machine-encoded medium that provides or participates in providing instructions to one or more processors. For example, a computer-readable medium may be one or more optical or magnetic memory disks, flash drives and cards, a read-only memory or a random access memory such as a DRAM, which typically constitutes the main memory. Such media excludes propagated signals, which are not tangible. Cached information is considered to be stored on a computer-readable medium. Common expedients of computer-readable media are well-known in the art and need not be described in detail here.

CONCLUSION

Disclosed is a general methodology for insulation defect identification in a generator core. The basic idea of using Chattock coil for defect identification is detailed and a model combining physical knowledge and empirical knowledge is proposed for defect location and severity prediction. To obtain the model parameters using efficient experimental testing, the Latin Hyper Cube method is proposed to perform the design of experiments and reduce the overall cost for experimental testing.

The foregoing detailed description is to be understood as being in every respect illustrative and exemplary, but not restrictive, and the scope of the disclosure herein is not to be determined from the description, but rather from the claims as interpreted according to the full breadth permitted by the patent laws. It is to be understood that various modifications will be implemented by those skilled in the art, without departing from the scope and spirit of the disclosure.

What is claimed is:

1. A method for detecting an insulation defect in a generator core, comprising:
   flowing an alternating excitation current at a first excitation frequency through an excitation winding adjacent the generator core to induce first eddy currents between laminations at the defect;
   measuring a first potentiometer voltage indicating magnetic flux caused by the first eddy currents induced at the first excitation frequency;
   flowing an alternating excitation current at a second excitation frequency through the excitation winding adjacent the generator core to induce second eddy currents between the laminations at the defect;
   measuring a second potentiometer voltage indicating magnetic flux caused by the second eddy currents induced at the second excitation frequency; and
   determining a severity of the defect and a depth of the defect using a response voltage relationship among the potentiometer voltages, the excitation frequencies, the severity of the defect, and the depth of the defect,
   wherein the response voltage relationship comprises fitting parameters and a term wherein the excitation frequency is raised to a function of a fitting parameter.

2. A method as in claim 1, wherein measuring the potentiometer voltage further comprises measuring a voltage of a Chattock potentiometer measuring magnetic potential difference between teeth of the generator core.

3. A method as in claim 2, wherein measuring a potentiometer voltage indicating magnetic flux caused by the eddy currents further comprises removing magnetic potential difference caused by the excitation current.

4. A method as in claim 1, wherein the response voltage relationship is $V = ks\omega^{1+\beta} \exp[\alpha d \ln \omega]$ wherein V is the potentiometer voltage, k, $\alpha$ and $\beta$ are fitting parameters, s is the severity of the defect, $\omega$ is the given excitation frequency and d is the depth of the defect.

5. A method as in claim 1, wherein the response voltage relationship includes an exponential function of the depth of the defect.

6. A method as in claim 5, wherein an operand of the exponential function is a logarithmic function of the excitation frequency.

7. A method as in claim 1, wherein the response voltage relationship includes a first-order function of the severity of the defect.

8. A method as in claim 1, wherein the severity of the defect is characterized by $$\frac{l_F}{R_F}$$

wherein $l_F$ is a total length of a defect-induced current and $R_F$ is a resistance of the defect-induced current.

9. A method as in claim 1, wherein the generator core is a generator stator core.

10. A non-transitory computer-readable medium having stored thereon computer readable instructions for detecting an insulation defect in a generator core, wherein execution of the computer readable instructions by a processor causes the processor to perform operations comprising:
   receiving a measurement of a first potentiometer voltage indicating magnetic flux caused by first eddy currents induced between laminations at the defect by flowing an alternating excitation current at a first excitation frequency through an excitation winding adjacent the generator core;
   receiving a measurement of a second potentiometer voltage indicating magnetic flux caused by second eddy currents induced between laminations at the defect by flowing an alternating excitation current at a second excitation frequency through the excitation winding adjacent the generator core; and
   determining a severity of the defect and a depth of the defect using a response voltage relationship among the potentiometer voltages, the excitation frequencies, the severity of the defect, and the depth of the defect, wherein the response voltage relationship comprises fitting parameters and a term wherein the excitation frequency is raised to a function of a fitting parameter.

11. A non-transitory computer-readable medium as in claim 10, wherein measuring the potentiometer voltage further comprises measuring a voltage of a Chattock potentiometer measuring magnetic potential difference between teeth of the generator core.

12. A non-transitory computer-readable medium as in claim 11, wherein measuring a potentiometer voltage indicating magnetic flux caused by the eddy currents further comprises removing magnetic potential difference caused by the excitation current.

13. A non-transitory computer-readable medium as in claim 10, wherein the response voltage relationship is $$V = ks\omega^{1+\beta} \exp[\alpha d \ln \omega]$$

wherein V is the potentiometer voltage, k, $\alpha$ and $\beta$ are fitting parameters, s is the severity of the defect, $\omega$ is the given excitation frequency and d is the depth of the defect.

14. A non-transitory computer-readable medium as in claim 10, wherein the response voltage relationship includes an exponential function of the depth of the defect.

15. A non-transitory computer-readable medium as in claim 14, wherein an operand of the exponential function is a logarithmic function of the excitation frequency.

16. A non-transitory computer-readable medium as in claim 10, wherein the response voltage relationship includes a first-order function of the severity of the defect.

17. A non-transitory computer-readable medium as in claim 10, wherein the severity of the defect is characterized by $$\frac{l_F}{R_F}$$

wherein $l_F$ is a total length of a defect-induced current and $R_F$ is a resistance of the defect-induced current.

18. A non-transitory computer-readable medium as in claim 10, wherein the generator core is a generator stator core.

19. A method for detecting an insulation defect in a generator core, comprising:
   flowing an alternating excitation current at a first excitation frequency through an excitation winding adjacent the generator core to induce first eddy currents between laminations at the defect;
   measuring a first potentiometer voltage indicating magnetic flux caused by the first eddy currents induced at the first excitation frequency;
   flowing an alternating excitation current at a second excitation frequency through the excitation winding adjacent the generator core to induce second eddy currents between the laminations at the defect;
   measuring a second potentiometer voltage indicating magnetic flux caused by the second eddy currents induced at the second excitation frequency; and
   determining a severity of the defect and a depth of the defect using a response voltage relationship among the potentiometer voltages, the excitation frequencies, the severity of the defect, and the depth of the defect,
   wherein the response voltage relationship comprises fitting parameters and an exponential function of the depth of the defect, wherein an operand of the exponential function is a logarithmic function of the excitation frequency.

* * * * *